(12) United States Patent
Ogai et al.

(10) Patent No.: US 11,344,710 B2
(45) Date of Patent: May 31, 2022

(54) MICRONEEDLE ARRAY

(71) Applicant: ASTI CORPORATION, Hamamatsu (JP)

(72) Inventors: Noriyuki Ogai, Hamamatsu (JP); Masahiro Takigawa, Kyoto (JP)

(73) Assignee: ASTI CORPORATION, Hamamatsu (JP)

( * ) Notice: Subject to any disclaimer, the term of this patent is extended or adjusted under 35 U.S.C. 154(b) by 196 days.

(21) Appl. No.: 16/498,863

(22) PCT Filed: Mar. 29, 2018

(86) PCT No.: PCT/JP2018/013078
§ 371 (c)(1),
(2) Date: Sep. 27, 2019

(87) PCT Pub. No.: WO2018/181639
PCT Pub. Date: Oct. 4, 2018

(65) Prior Publication Data
US 2020/0046957 A1 Feb. 13, 2020

(30) Foreign Application Priority Data

Mar. 31, 2017 (JP) .............................. JP2017-069468
Jul. 28, 2017 (JP) .............................. JP2017-146091

(51) Int. Cl.
*A61M 37/00* (2006.01)

(52) U.S. Cl.
CPC ... *A61M 37/0015* (2013.01); *A61M 2037/003* (2013.01); *A61M 2037/0023* (2013.01); *A61M 2037/0053* (2013.01)

(58) Field of Classification Search
CPC ...... A61M 37/0015; A61M 2037/0023; A61M 2037/003; A61M 2037/0053
See application file for complete search history.

(56) References Cited

U.S. PATENT DOCUMENTS

| 2013/0218084 A1* | 8/2013 | Tamaru | ............. | A61M 37/0015 604/173 |
| 2014/0236075 A1* | 8/2014 | Sugimura | ............... | B29C 67/00 604/46 |

FOREIGN PATENT DOCUMENTS

| JP | 2003-52672 A | 2/2003 | | |
| JP | 2012-157406 A | 8/2012 | | |
| JP | 2012157406 A | * 8/2012 | ........ | A61M 37/0015 |

(Continued)

OTHER PUBLICATIONS

PCT/ISA/210, "International Search Report for International Application No. PCT/JP2018/013078," dated Apr. 24, 2018.

*Primary Examiner* — Amber R Stiles
(74) *Attorney, Agent, or Firm* — Manabu Kanesaka

(57) ABSTRACT

The purpose of the present invention is to provide a microneedle array and a microneedle manufacturing method, which improves medical solution delivery efficiency and facilitates manufacturing. The microneedle array is provided with a first divisional element, a second divisional element to be bonded to the first divisional element, a longitudinal passage formed between the first divisional element and the second divisional element bonded to each other; and a horizontal hole, having an orifice on a lateral side and formed in a direction parallel to a bonding surface of the first divisional element with the second divisional element, and communicating to the longitudinal passage.

18 Claims, 12 Drawing Sheets

(56) References Cited

FOREIGN PATENT DOCUMENTS

| | | |
|---|---|---|
| JP | 2015-198786 A | 11/2015 |
| KR | 20090025937 A | 3/2009 |
| WO | 2013/061825 A1 | 5/2013 |

\* cited by examiner

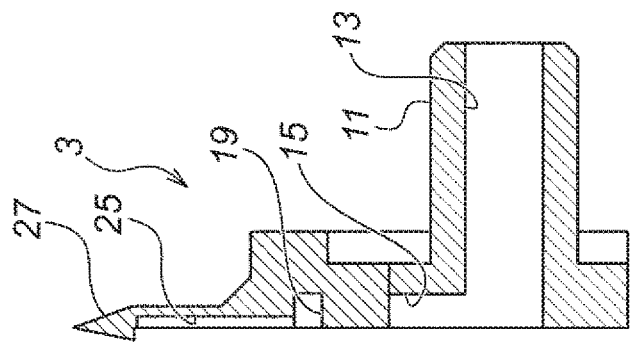
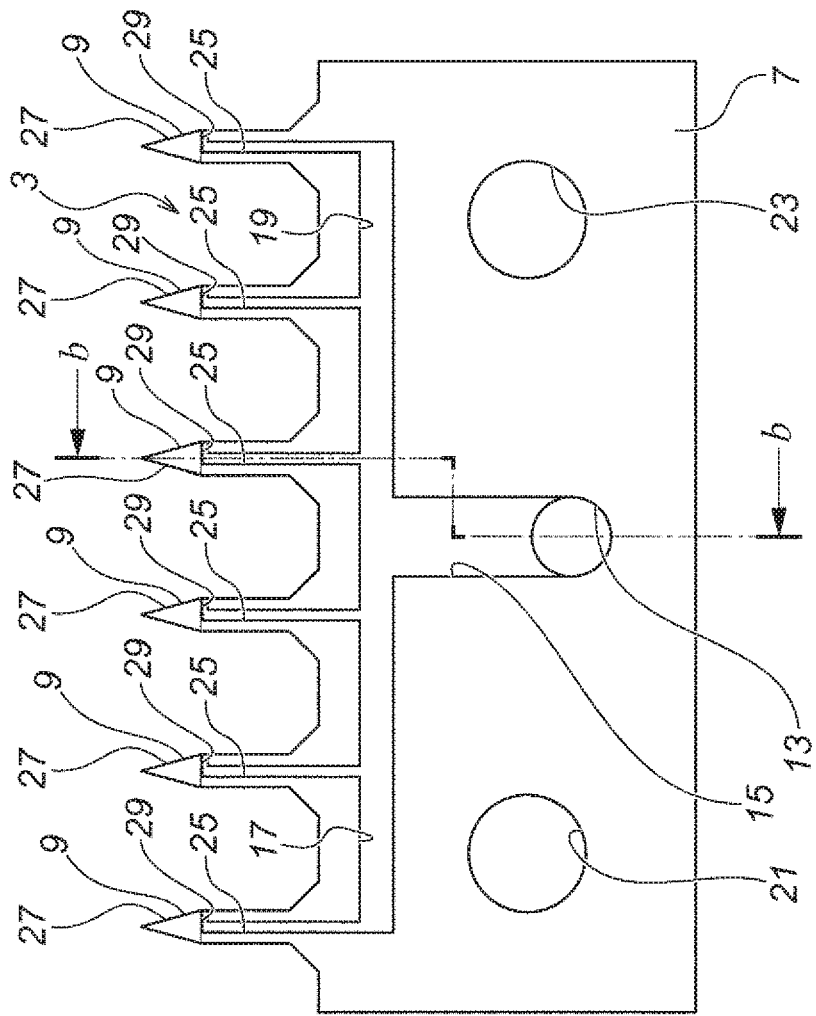

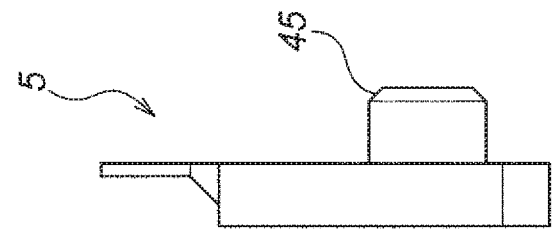
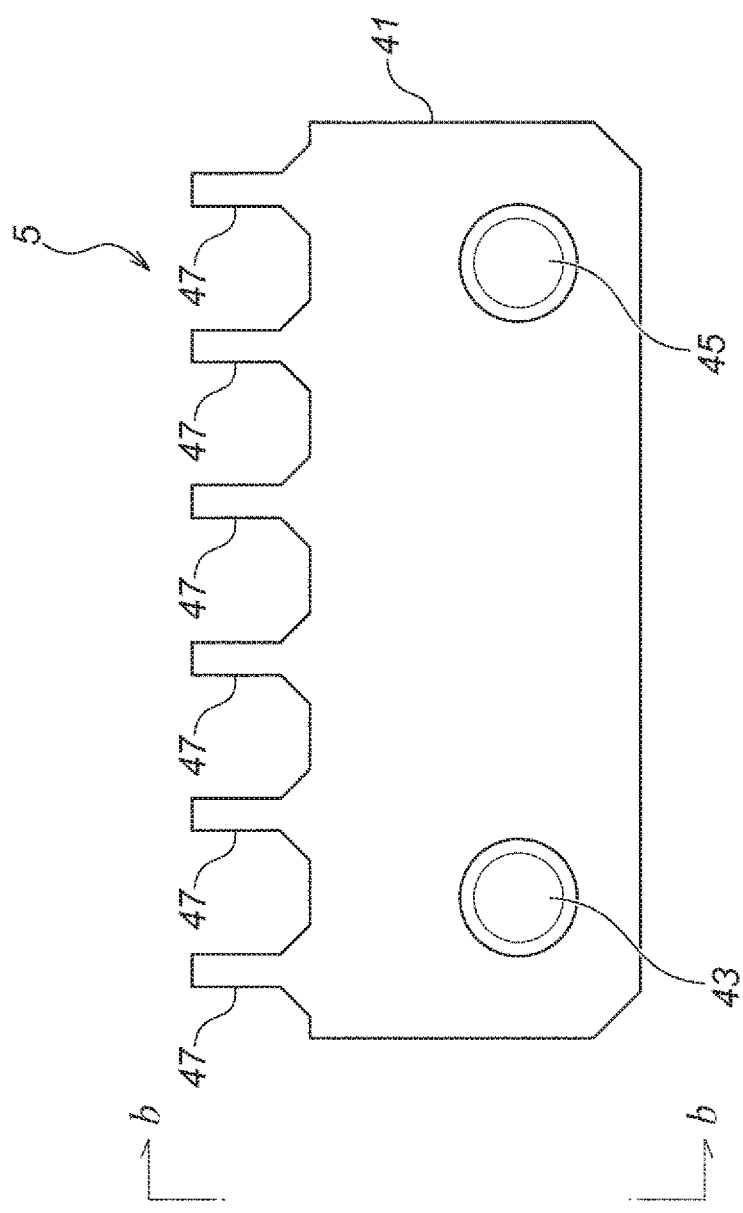

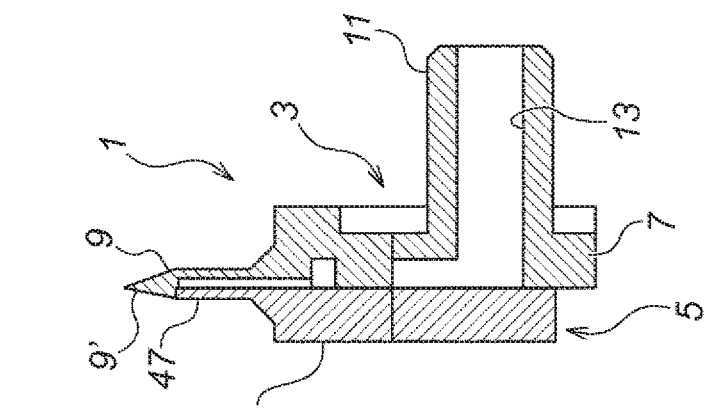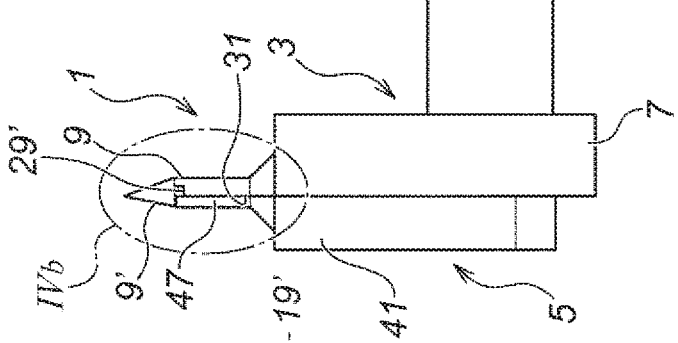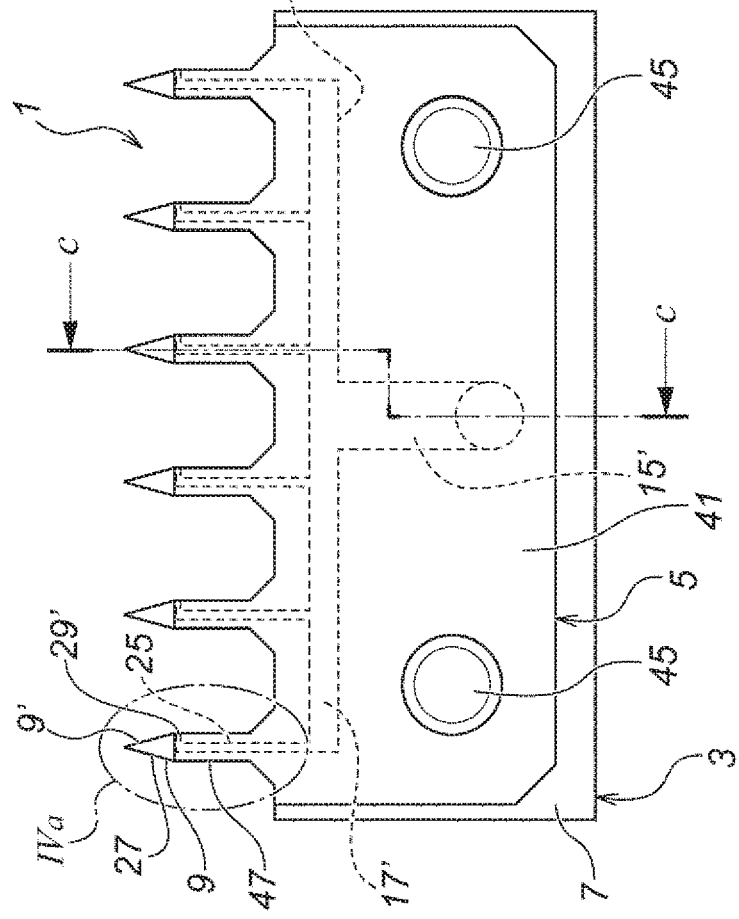

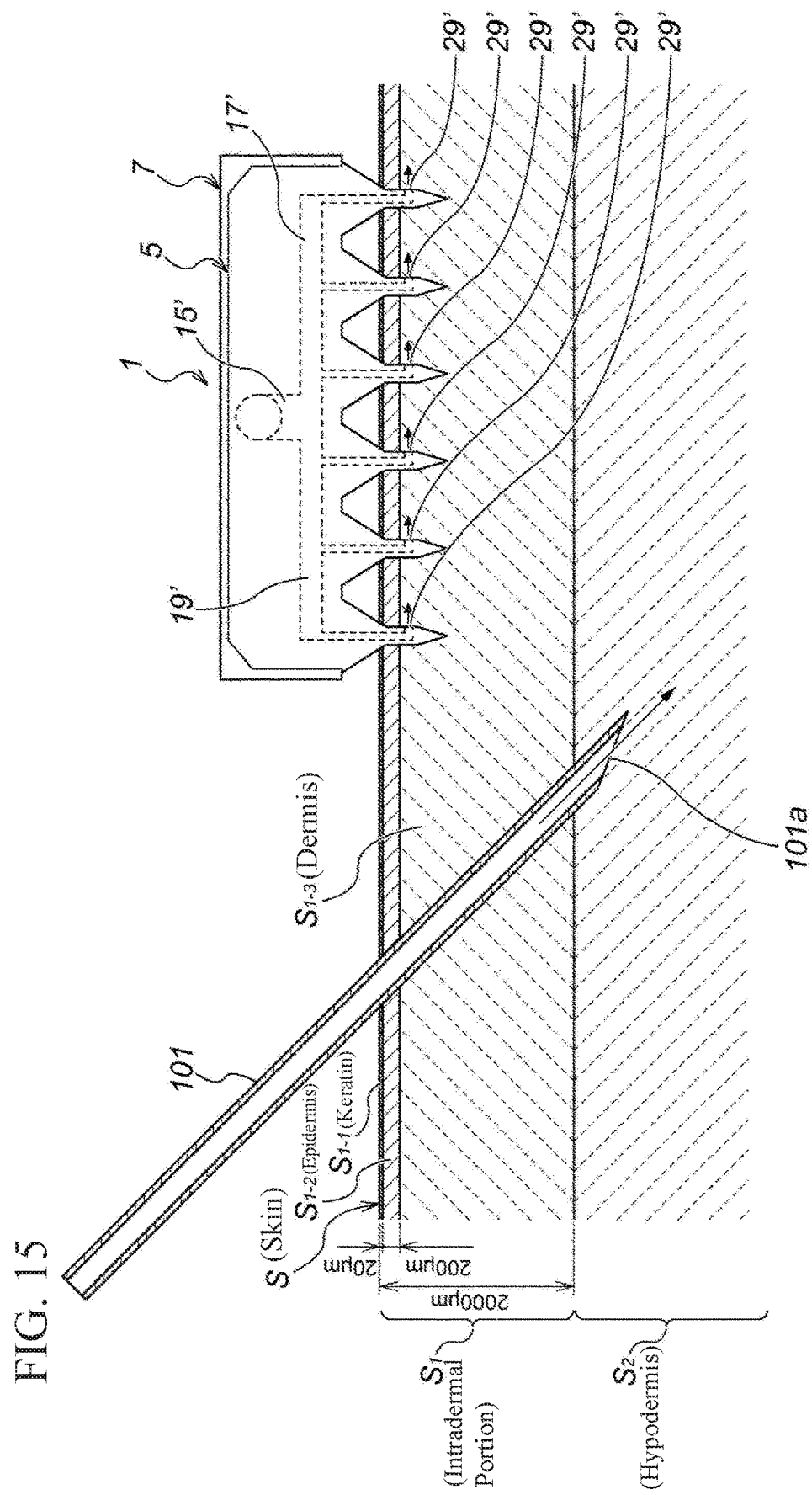

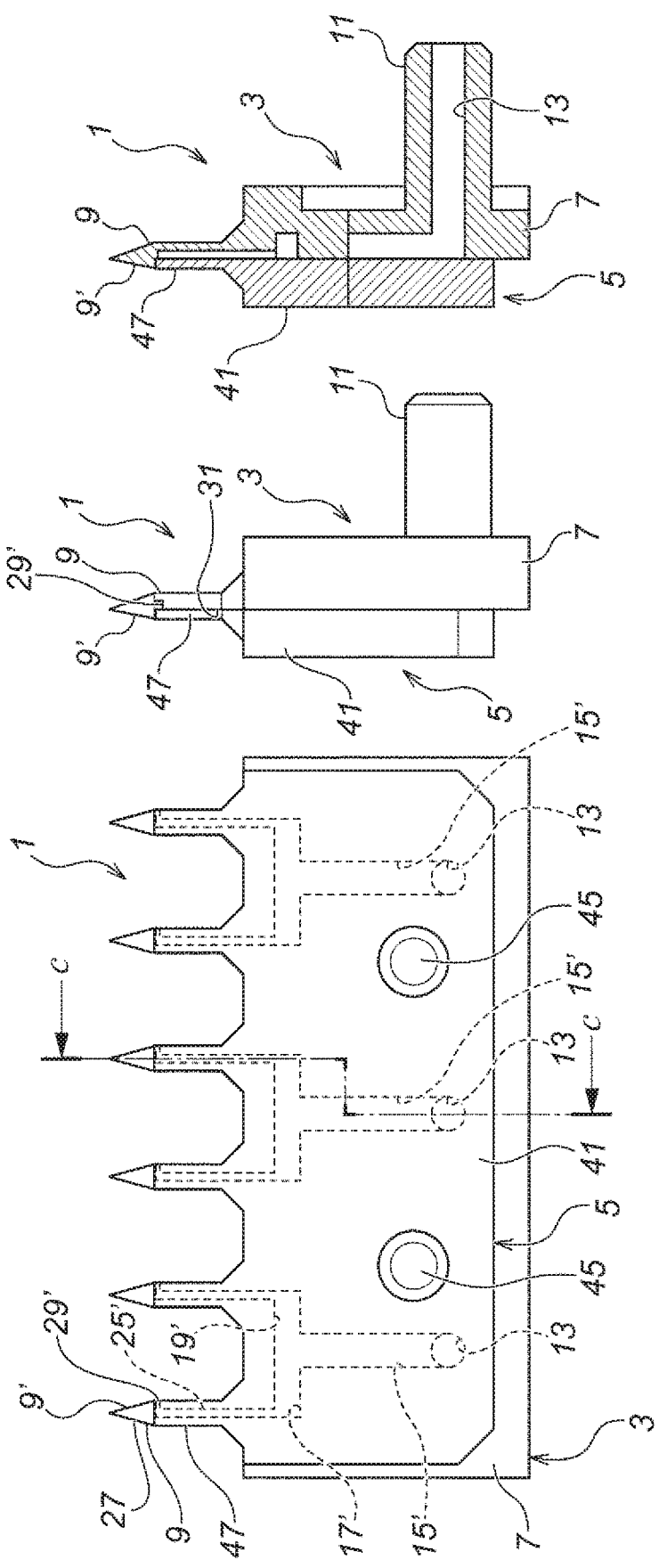

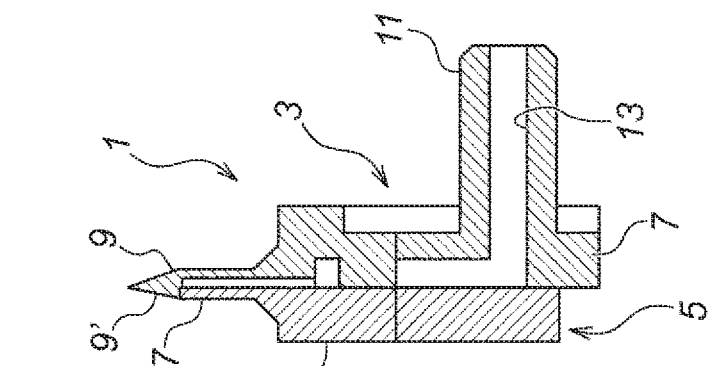
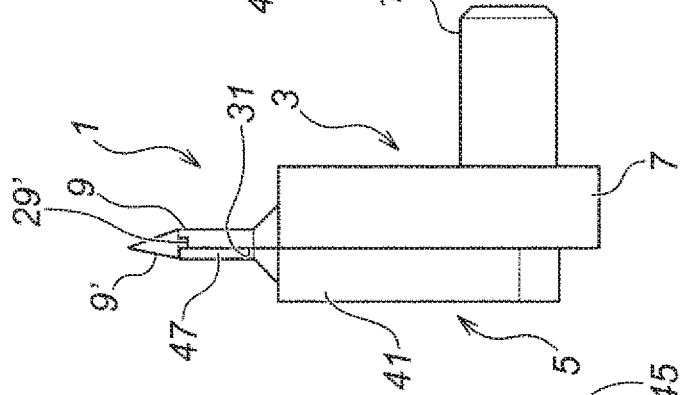
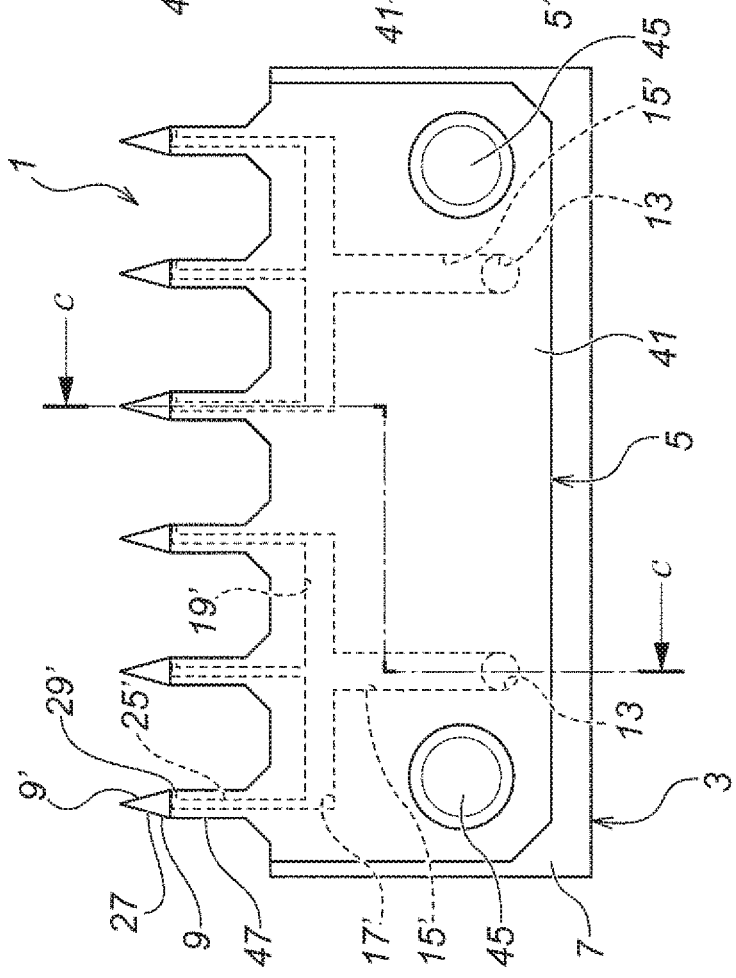
FIG. 17(a)
FIG. 17(b)
FIG. 17(c)

MICRONEEDLE ARRAY

RELATED APPLICATIONS

The present application is National Phase of International Application No. PCT/JP2018/013078 filed Mar. 29, 2018, and claim priorities from Japanese Applications No. 2017-069468, filed Mar. 31, 2017 and No. 2017-146091, filed Jul. 28, 2017, the disclosure of which is hereby incorporated by reference herein in its entirety.

TECHNICAL FIELD

The present invention relates to a microneedle array and a production method for microneedle array, and more specifically, relates to those which improve medical solution delivery efficiency and facilitate manufacturing thereof.

BACKGROUND ART

As disclosures of structures of microneedle arrays, for example, Patent Document 1 and Patent Document 2 are known.

In these documents, a fine needle array disclosed in Patent Document 1 substantially has the following structure: first, there are a first substrate and a second substrate, and the first substrate and the second substrate are bonded to each other, and a first passage is formed therebetween. The first passage has a structure that the tip thereof has an orifice. Thus, a tip part formed by bonding the first substrate and the second substrate punctures into the skin, and a medical solution is injected intradermally or subcutaneously from the tip part of the first substrate.

According to the invention as disclosed in Patent Document 1, since the first passage has the structure that the tip part thereof has been formed in a state of having the orifice, when the puncture is performed, the skin tissue, etc., may intrude into the first passage, whereby the first passage is clogged, which would result in a problematic situation that the efficiency in medical solution delivery is deteriorated. In particular, in the case of needles made of resin, since the tip strength is not sufficient, there has been a risk that the shape could be deformed at the time of puncturing.

On the other hand, according to Patent Document 2, there is a structure that a horizontal hole is formed at the tip part of the microneedle, so that the medical solution may be injected subcutaneously from this horizontal hole.

According to this horizontal hole, the problem concerned in the case of the first passage of Patent Document 1, namely the deterioration of medical solution delivery efficiency caused by clogging, may be solved.

REFERENCE DOCUMENTS OF CONVENTIONAL ART

Patent Document(S)

Patent Document 1: Official Gazette, KRA-20090025937.
Patent Document 2: Official Gazette, JP 2003-52672 A.

SUMMARY OF THE INVENTION

Problems to be Solved by Invention

However, the above structures of the conventional arts have the following problems:

First, as described in the invention of Patent Document 2, where the horizontal hole is formed at the tip part of the microneedle so that medical solution may be injected subcutaneously via this horizontal hole, although it is possible to solve the concerned problem of deterioration of medical solution delivery efficiency caused by clogging at the time of puncturing, in fact, it is not easy to form the horizontal hole at the fine-shaped tip part of microneedle, and in particular, in the case of the invention as described in Patent Document 2, the horizontal hole is formed by "stereolithography," of which work being difficult and requiring a long period of time.

Moreover, since the material is limited to photo-curable resin, there have been other problems, such as difficulties in securing of the strength and the biosafety required as the microneedle.

In the light of the above problems, it is an object of the present invention to provide a microneedle array and a microneedle array manufacturing method, which improve medical solution delivery efficiency and facilitate manufacturing thereof.

Means to Solve the Problem

To achieve the objects mentioned above, according to the first aspect of the present invention, a microneedle array is provided with: a first divisional element; a second divisional element to be bonded to the first divisional element; a longitudinal passage formed between the first divisional element and the second divisional element bonded to each other; and a horizontal hole, having an orifice on a lateral side and formed in a direction parallel to a bonding surface of the first divisional element with the second divisional element bonded to each other, and communicating to the longitudinal passage.

Moreover, according to the microneedle array of the second aspect, with regard to the microneedle array of the first aspect, the horizontal hole is positioned to be located in a region within 2,000 μm intradermally during puncturing.

Moreover, according to the microneedle array of the third aspect, with regard to the microneedle array of the second aspect, the horizontal hole is positioned to be located in a region within 1,000 μm intradermally during puncturing.

Moreover, according to the microneedle array of the fourth aspect, with regard to the microneedle array of the third aspect, the horizontal hole is positioned to be located in a region within 500 μm intradermally during puncturing.

Moreover, according to the microneedle array of the fifth aspect, with regard to the microneedle array as claimed in any one of the first to fourth aspects, the first divisional element comprises, an element main body, and a first microneedle element formed on the element main body; the second divisional element comprises, an element main body, and a second microneedle element formed on the element main body and constitutes a microneedle by bonding to the first microneedle element; and the horizontal hole is formed between the first microneedle element and the second microneedle element.

Moreover, according to the microneedle array of the sixth aspect, with regard to the microneedle array of the fifth aspect, the microneedle is provided in a plural number.

Moreover, according to the microneedle array of the seventh aspect, with regard to the microneedle array of the fifth or sixth aspect, any one component among the first microneedle element and the second microneedle element is provided with a tip part serving as the complete microneedle, and any counterpart component has a length as short as the length of the tip part.

Moreover, according to the microneedle array of the eighth aspect, with regard to the microneedle array of the seventh aspect, the tip part of any one component is in a shape of arrowhead.

Moreover, according to the microneedle array of the ninth aspect, with regard to the microneedle array as claimed in any one of the fifth to eighth aspects, the length of each of the microneedles is ununified.

Moreover, according to the microneedle array of the tenth aspect, with regard to the microneedle array as claimed in any one of the first to ninth aspects, the longitudinal passage is formed by forming a longitudinal passage groove in any one component among the first divisional element and the second divisional element, and by enclosing the longitudinal passage groove by any counterpart component.

Moreover, according to the microneedle array of the eleventh aspect, with regard to the microneedle array as claimed in any one of the first to ninth aspects, the longitudinal passage is formed by forming longitudinal passage grooves in both the first divisional element and the second divisional element, respectively, and by bonding the first divisional element and the second divisional element to each other.

Moreover, according to the microneedle array of the twelfth aspect, with regard to the microneedle array as claimed in any one of the first to eleventh aspects, the horizontal hole is formed by forming a horizontal hole groove in any one component among the first divisional element and the second divisional element, and by enclosing the horizontal hole groove by any counterpart component.

Moreover, according to the microneedle array of the thirteenth aspect, with regard to the microneedle array as claimed in any one of the first to eleventh aspects, the horizontal hole is formed by forming horizontal hole grooves in both the first divisional element and the second divisional element, respectively, and by bonding the first divisional element and the second divisional element to each other.

Moreover, according to the microneedle array of the fourteenth aspect, with regard to the microneedle array as claimed in any one of the first to thirteenth aspects, the horizontal hole is formed to have an orifice on any one lateral side, in a direction parallel to the bonding surface.

Moreover, according to the microneedle array of the fifteenth aspect, with regard to the microneedle array as claimed in any one of the first to thirteenth aspects, the horizontal hole is formed to have orifices penetrating through both lateral sides, in a direction parallel to the bonding surface.

Moreover, according to the microneedle array of the sixteenth aspect, with regard to the microneedle array as claimed in any one of the first to fifteenth aspects, the horizontal hole is formed to have an orifice on a lateral side, in a direction intersecting with the bonding surface at an arbitrary angle.

Moreover, according to the microneedle array of the seventeenth aspect, with regard to the microneedle array as claimed in any one of the first to sixteenth aspects, the horizontal hole is formed in a plural number.

Moreover, according to the microneedle array of the eighteenth aspect, with regard to the microneedle array of the seventeenth aspect, each of the plurality of horizontal holes is provided at a different position along the direction of puncture.

Moreover, according to the microneedle array of the nineteenth aspect, with regard to the microneedle array of the seventeenth or eighteenth aspect, a plurality of horizontal holes is formed in one microneedle.

Moreover, according to the microneedle array of the twentieth aspect, with regard to the microneedle array as claimed in any one of the first to nineteenth aspects, the horizontal hole is formed to become gradually thinner toward the orifice.

Moreover, according to the microneedle array of the twenty-first aspect, with regard to the microneedle array as claimed in any one of the first to twentieth aspects, the horizontal hole is formed to be oriented in an inclined direction, from a position orthogonal to the longitudinal passage, toward a tip side.

Moreover, according to a microneedle array manufacturing method of the twenty-second aspect, a first divisional element and a second divisional element are bonded to each other, whereby a longitudinal passage is formed between the first divisional element and the second divisional element bonded to each other, and a horizontal hole is formed to have an orifice facing toward a lateral side of a bonding surface of the first divisional element with the second divisional element bonded to each other, so as to communicate to the longitudinal passage.

And moreover, according to the microneedle array manufacturing method of the twenty-third aspect, with regard to the microneedle array manufacturing method of the twenty-second aspect, further horizontal hole is also formed in a direction intersecting with the bonding surface at an arbitrary angle.

Effect of the Invention

As described above, according to the first asect of the present invention, the microneedle array is provided with: a first divisional element; a second divisional element to be bonded to the first divisional element; a longitudinal passage formed between the first divisional element and the second divisional element bonded to each other; and a horizontal hole, having an orifice on a lateral side and formed in a direction parallel to a bonding surface of the first divisional element with the second divisional element bonded to each other, and communicating to the longitudinal passage. Therefore, it is possible to improve the efficiency in medical solution delivery, and also to facilitate the manufacturing thereof.

Moreover, according to the microneedle array of the second aspect, with regard to the microneedle array of the first aspect, it is possible to feed medical solution efficiently, to various cells such as the immune cells, concentrating in the region of the epidermis, and also to the lymphatic vessels around the capillary vessels, concentrating in the region of the dermis.

Since the horizontal hole is positioned to be located in a region within 2,000 µm intradermally during puncturing, it is possible to feed the medical solution efficiently, to various cells such as the immune cells, concentrating in the region of the epidermis, and also to the lymphatic vessels around the capillary vessels, concentrating in the region of the dermis.

Moreover, according to the microneedle array of the third aspect, with regard to the microneedle array of the second aspect, the horizontal hole is positioned to be located in a region within 1,000 µm intradermally during puncturing. Therefore, it is possible to feed the medical solution efficiently, to various cells such as the immune cells, concentrating in the region of the epidermis, and also to the lymphatic vessels around the capillary vessels, concentrating in the region of the dermis.

Moreover, according to the microneedle array of to the fourth aspect, with regard to the microneedle array of the third aspect, the horizontal hole is positioned to be located in a region within 500 µm intradermally during puncturing. Therefore, it is possible to feed the medical solution efficiently, to various cells such as the immune cells, concentrating in the region of the epidermis, and also to the lymphatic vessels around the capillary vessels, concentrating in the region of the dermis.

Moreover, according to the microneedle array of the fifth aspect, with regard to the microneedle array as claimed in any one claim of the first to fourth aspects, the first divisional element comprises, an element main body, and a first microneedle element formed on the element main body; the second divisional element comprises, an element main body, and a second microneedle element formed on the element main body and constitutes a microneedle by bonding to the first microneedle element; and the horizontal hole is formed between the first microneedle element and the second microneedle element. Therefore, it is possible to improve the medical solution delivery, and also to facilitate the manufacturing thereof.

Moreover, according to the microneedle array of the sixth aspect, with regard to the microneedle array of the fifth aspect, the microneedle is provided in a plural number. Therefore, it is possible to improve the medical solution delivery, and also to facilitate the manufacturing thereof.

Moreover, according to the microneedle array of the seventh aspect, with regard to the microneedle array of the fifth or sixth aspect, any one component among the first microneedle element and the second microneedle element is provided with a tip part serving as the complete microneedle, and any counterpart component has a length as short as the length of the tip part. Therefore, it is possible to improve the strength of the tip part serving as the microneedle.

Moreover, according to the microneedle array of the eighth aspect, with regard to the microneedle array of the seventh aspect, the tip part of any one component is in a shape of arrowhead. Therefore, for example, with the arrangement of the height of the second divisional element to be substantially equal to or lower than that of the arrowhead, it is possible to avoid the resistance against puncture or the risk of drop-off.

Moreover, according to the microneedle array of the ninth aspect, with regard to the microneedle array as claimed in any one of the fifth to eighth aspects, the length of each of the microneedles is ununified. Therefore, it is possible to expand the diffusion depth of the medical solution.

Moreover, according to the microneedle array of the tenth aspect, with regard to the microneedle array as claimed in any one of the first to ninth aspects, the longitudinal passage is formed by forming a longitudinal passage groove in any one component among the first divisional element and the second divisional element, and by enclosing the longitudinal passage groove by any counterpart component. Therefore, it is possible to form the longitudinal passage easily.

Moreover, according to the microneedle array of the eleventh aspect, with regard to the microneedle array as claimed in any one of the first to ninth aspects, the longitudinal passage is formed by forming longitudinal passage grooves in both the first divisional element and the second divisional element, respectively, and by bonding the first divisional element and the second divisional element to each other. Therefore, also in this case, it is possible to form the longitudinal passage easily.

Moreover, according to the microneedle array of the twelfth aspect, with regard to the microneedle array as claimed in any one of the first to eleventh aspects, the horizontal hole is formed by forming a horizontal hole groove in any one component among the first divisional element and the second divisional element, and by enclosing the horizontal hole groove by any counterpart component Therefore, it is possible to form the horizontal hole easily.

Moreover, according to the microneedle array of the thirteenth aspect, with regard to the microneedle array as claimed in any one of first to eleventh aspects, the horizontal hole is formed by forming horizontal hole grooves in both the first divisional element and the second divisional element, respectively, and by bonding the first divisional element and the second divisional element to each other. Therefore, also in this case, it is possible to form the horizontal hole easily.

Moreover, according to the microneedle array of the fourteenth aspect, with regard to the microneedle array as claimed in any one of the first to thirteenth aspects, the horizontal hole is formed to have an orifice on any one lateral side, in a direction parallel to the bonding surface. Therefore, the above effect can be accomplished more securely.

Moreover, according to the microneedle array of the fifteenth aspect, with regard to the microneedle array as claimed in any one of the first to thirteenth aspects, the horizontal hole is formed to have orifices penetrating through both lateral sides, in a direction parallel to the bonding surface. Therefore, the above effect can be accomplished more securely.

Moreover, according to the microneedle array of the sixteenth aspect, with regard to the microneedle array as claimed in any one of the first to fifteenth aspects, the horizontal hole is formed to have an orifice on a lateral side, in a direction intersecting with the bonding surface at an arbitrary angle. Therefore, also with this structure, it is possible to improve the efficiency in medical solution delivery.

Moreover, according to the microneedle array of the seventeenth aspect, with regard to the microneedle array of the first to sixteen aspects, the horizontal hole is formed in a plural number. Therefore, the above effect, in particular the improvement of efficiency in medical solution delivery, can be accomplished more effectively.

Moreover, according to the microneedle array of the eighteenth aspect, with regard to the microneedle array of the seventeenth aspect, each of the plurality of horizontal holes is provided at a different position along the direction of puncture. Therefore, also with this structure, it is possible to improve the efficiency in medical solution delivery more effectively.

Moreover, according to the microneedle array of the nineteenth aspect, with regard to the microneedle array of the seventeenth or eighteenth aspect, a plurality of horizontal holes is formed in one microneedle. Therefore, also with this structure, it is possible to improve the efficiency in medical solution delivery more effectively.

Moreover, according to the microneedle array of the twentieth aspect, with regard to the microneedle array of the first to nineteenth aspects, the horizontal hole is formed to become gradually thinner toward the orifice. Therefore, the above effect can be facilitated.

Moreover, according to the microneedle array of the twenty-first aspect, with regard to the microneedle array of the first to wentieth aspects, the horizontal hole is formed to be oriented in an inclined direction, from a position orthogonal to the longitudinal passage, toward a tip side. Therefore, the above effect can be facilitated.

Moreover, according to a microneedle array manufacturing method of the twenty-second aspect, a first divisional element and a second divisional element are bonded to each other, whereby a longitudinal passage is formed between the first divisional element and the second divisional element bonded to each other, and a horizontal hole is formed to have an orifice facing toward a lateral side of a bonding surface of the first divisional element with the second divisional element bonded to each other, so as to communicate to the longitudinal passage. Therefore, it is possible to provide the microneedle array easily, having the horizontal hole formed to have the orifice facing toward the lateral side of the bonding surface.

And moreover, according to the microneedle array manufacturing method of the twenty-third aspect, with regard to the microneedle array manufacturing method of the twenty-first aspect, further horizontal hole is also formed in a direction intersecting with the bonding surface at an arbitrary angle. Therefore, it is possible to manufacture the horizontal hole easily, also in the direction intersecting with the bonding surface at an arbitrary angle.

BRIEF DESCRIPTION OF DRAWINGS

FIG. 1(a) is a front view of a first divisional element, and FIG. 1(b) is a sectional view as seen by the line b-b of FIG. 1(a), according to a first embodiment of the present invention.

FIG. 2(a) is a front view of a second divisional element, and FIG. 2(b) is a view as seen by the arrows b-b of FIG. 2(a), according to a first embodiment of the present invention.

FIG. 3(a) is a front view of a microneedle array, FIG. 3(b) is a side view of the microneedle array, and FIG. 3(c) is a sectional view as seen by the line c-c of FIG. 3(a), according to a first embodiment of the present invention.

FIG. 15 is a sectional view comparing between a state in which a microneedle array punctures intradermally and a state in which a syringe needle punctures subcutaneously, according to a twelfth embodiment of the present invention.

FIG. 16(a) is a front view of a microneedle array, FIG. 16(b) is a side view of the microneedle array, and FIG. 16(c) is a sectional view as seen by the line c-c of FIG. 16(a), according to a thirteenth embodiment of the present invention.

FIG. 17(a) is a front view of a microneedle array, FIG. 17(b) is a side view of the microneedle array, and FIG. 17(c) is a sectional view as seen by the line c-c of FIG. 17(a), according to a fourteenth embodiment of the present invention.

MODE(S) FOR CARRYING OUT THE INVENTION

Figure 4A:
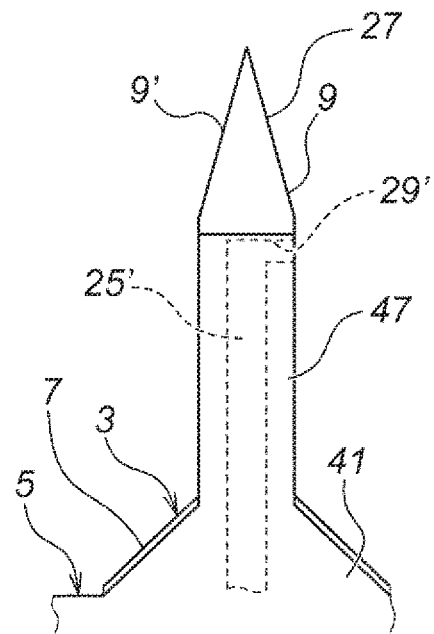
FIG. 4(a) is an expanded view of a part VIa of FIG. 3(a)

Now, a first embodiment of the present invention will be explained as below, with reference to FIG. 1 to FIG. 4. As illustrated in FIG. 3, a microneedle array 1 according to the present embodiment has a structure that a first divisional element 3 and a second divisional element 5 are bonded to each other.

The first divisional element 3 has a structure as illustrated in FIG. 1. First, there is an element main body 7, and the element main body 7 has a plurality of (in the present embodiment, six) first microneedle elements 9 formed integrally.

Note that, although the number of microneedles (shown by reference numeral 9' in FIG. 3 and FIG. 4) is not specifically limited, the preferable number is about three to twelve. Moreover, the length of the microneedle 9' is preferably 1 mm or less, and the thickness thereof is preferably about 0.1 mm to 0.3 mm.

A boss 11 is protrusively provided at the center of the element main body 7, and a medical solution feeding passage 13 is formed inside of the boss 11. The boss 11 is used for the connection with any device such as tube, syringe, pump, liquid forwarding connector, etc. Moreover, a medical solution feeding passage groove 15 is formed in the element main body 7, and two medical solution feed branching grooves 17, 19 are formed in series in the medical solution feeding passage groove 15.

Moreover, it is also possible to connect the passage of each of the microneedles 9' directly to the medical solution feeding passage 13, without using the medical solution feed branching grooves 17, 19. Moreover, in such a structure, it is preferable to adjust the length of each of the passages so that the medical solution can be discharged equally.

Since the bonding surface is a plane surface, there is no special difficulty in terms of mold preparation and resin forming, and accordingly, various passage designs as described above may be applied.

Further, positioning holes 21, 23 are formed, respectively, in the element main body 7.

Moreover, a longitudinal passage groove 25 is formed in each of the plurality of first microneedle elements 9 as described above, and a part of the longitudinal passage groove 25 extends toward the side of the element main body 7, and communicates with the two medical solution feed branching grooves 17, 19 as described above.

Moreover, as illustrated in FIG. 1(b), a tip part 27 of the first microneedle element 9 is directly formed to become a tip part serving as the microneedle 9', in a bulging shape at a corresponding length toward the left side of the drawing. Moreover, the tip part 27 is in a shape of arrowhead, which is a shape sharpening toward the tip side, and at the same time, which is a shape bulging toward the second divisional element 5.

Moreover, a horizontal hole groove 29 is continuously formed at the tip end of the longitudinal passage groove 25. The horizontal hole groove 29 communicates with the longitudinal passage groove 25, formed to have an orifice facing toward one end side (the right side of FIG. 1(a)) in the direction parallel to a bonding surface 31 of the first divisional element 3.

On the other hand, the second divisional element 5 has the following structure. As illustrated in FIG. 2, first, there is an element main body 41, and positioning projections 43, 45 are protrusively provided, respectively, on the element main body 41. Moreover, a plurality of (in the present embodiment, six) second microneedle elements 47 is integrally formed in the element main body 41. As illustrated in FIG. 2(b), the second microneedle element 47 is formed in a shape of flat plate. Moreover, as described above, since the tip part 27 of the first microneedle element 9 of the first divisional element 3 includes the complete shape of the tip part serving as the microneedle 9', the length of the second microneedle element 47 is as short as the corresponding amount.

Thus, as illustrated in FIG. 3, the bonding of the first divisional element 3 with the second divisional element 5, each having the structure as described above, constitutes the microneedle array 1. At that time, the positioning projections 43, 45 on the side of the second divisional element 5 are inserted, respectively, into the positioning holes 21, 23 of the first divisional element 3. Moreover, the medical solution feeding groove 15, the medical solution feed branching grooves 17, 19, the longitudinal passage groove 25 and horizontal hole groove 29 of the first divisional element 3 are enclosed by the second divisional element 5, whereby a medical solution feeding passage 15', medical solution branching passages 17', 19', longitudinal passages 25' and horizontal holes 29' are formed. Moreover, the microneedle 9' is formed by the first microneedle element 9 and the second microneedle element 47.

Figure 4B:
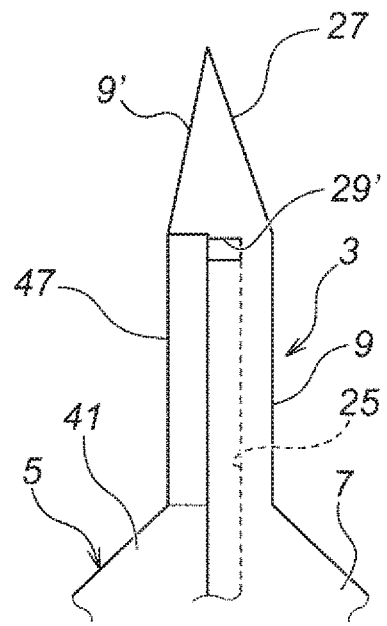
FIG. 4(b) is an expanded view of a part VIb of FIG. 3(b), according to the first embodiment of the present invention.

For reference, FIG. 4 illustrates an expanded view of the tip part of the microneedle 9' after the bonding is completed.

Moreover, as a material for the microneedle array 1, any biocompatible resin may preferably be used, and mass-production such as by injection molding is preferable.

Moreover, as for a method of bonding, heat bonding, laser bonding, ultrasonic bonding, adhesive, etc., may be used.

According to the present embodiment as described above, the following effects may be accomplished.

First, it is possible to improve the efficiency in medical solution delivery. This is because of the structure that the medical solution is injected into the skin via the horizontal hole 29', whereby any clogging caused by skin tissue, etc., may be prevented at the time of puncturing.

Moreover, it is possible to facilitate the manufacturing thereof. This is because of the structure that, the horizontal hole 29' is provided in a state to be oriented in the direction parallel to the bonding surface of the first divisional element 3 with the second divisional element 5. In particular, this is because of the structure that, in the case of the present embodiment, by forming the horizontal hole groove 29 in the microneedle element 9 of the first divisional element 3, with the simple enclosure by bonding of the second divisional element 5 therewith, the horizontal hole 29' can be formed.

The same effect applies to the longitudinal passage 25'. This is because, by forming the longitudinal passage groove 25 in the microneedle element 9 of the first divisional element 3, with the simple enclosure by bonding of the second divisional element 5 therewith, the longitudinal passage 25' can be formed.

The same effect applies to the medical solution feed branching passages 17', 19' and the medical solution feeding passage 15'. This is because, by forming the medical solution feed branching passage grooves 17, 19 and the medical solution feeding passage groove 15, respectively, in the microneedle element 9 of the first divisional element 3, with the simple enclosure by bonding of the second divisional element 5 therewith, the medical solution feed branching passages 17', 19', and the medical solution feeding passage 15', respectively, can be formed.

Moreover, the tip part 27 of the microneedle element 9 of the first divisional element 3 in itself is the tip part serving as the microneedle 9', and since this part is formed without special bonding, it is possible to improve the strength of the tip part of the microneedle 9'.

Moreover, since the tip part is not in the bonded structure, it is possible to prevent from being taken off unintendedly at the time of puncturing.

Moreover, since the tip part of the first divisional element is in a shape of arrowhead, and with the arrangement of the height of the second divisional element to be substantially equal to or lower than that of the arrowhead, it is possible to avoid the resistance against puncture or the risk of drop-off.

Figure 5:
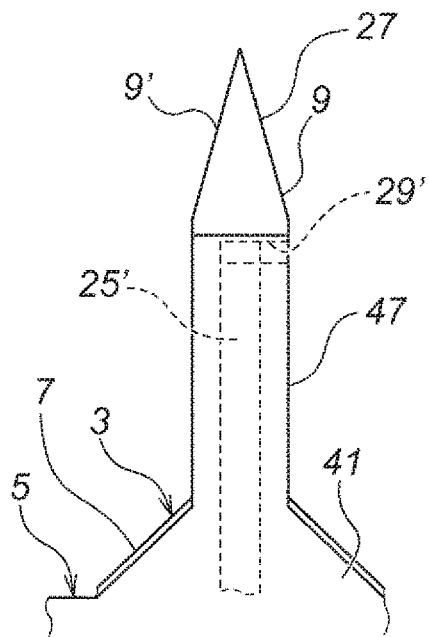
FIG. 5 is a partial front view of a microneedle array according to a second embodiment of the present invention.

Next, a second embodiment of the present invention will be explained with reference to FIG. 5. In the case of the first embodiment as described above, the longitudinal passage groove 25 and the horizontal hole groove 29 are formed on the side of the first divisional element 3, and in the case of the second embodiment, the longitudinal passage groove 25 is formed on the side of the second divisional element 5.

The other structure is substantially the same as that of the first embodiment as described above, so the same reference numerals will be allotted to the same parts in the drawing, and the explanation thereof will be omitted.

According to this structure, it is also possible to accomplish substantially the same effects as those of the first embodiment.

Figure 6:
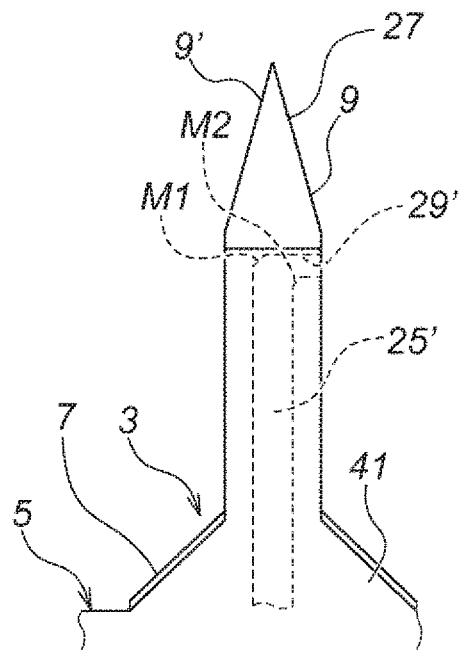
FIG. 6 is a partial front view of a microneedle array according to a third embodiment of the present invention.

Next, a third embodiment of the present invention will be explained with reference to FIG. 6. In the case of the third embodiment, in the structure of the first embodiment, chamfering has been applied to corners of boundary sections between the longitudinal passage groove 25 and the horizontal hole groove 29. Reference numerals M1, M2 in the drawing show chamfered parts, respectively.

The other structure is substantially the same as that of the first embodiment as described above, so the same reference numerals will be allotted to the same parts in the drawing, and the explanation thereof will be omitted.

According to this structure, it is also possible to accomplish substantially the same effects as those of the first embodiment, and in addition, because of the chamfering, the flow of the medical solution becomes smoother, whereby it is possible to further improve the efficiency in medical solution delivery.

Figure 7:
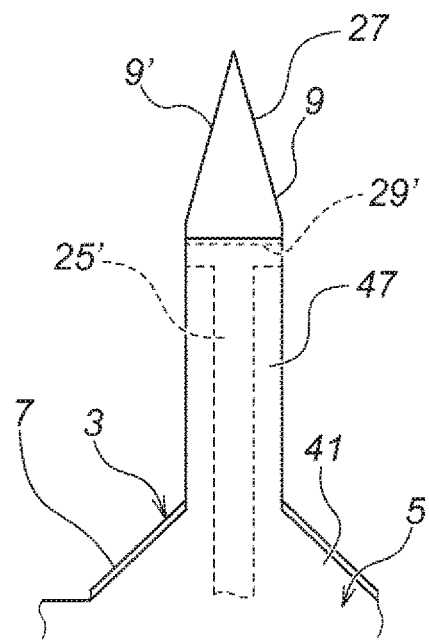
FIG. 7 is a partial front view of a microneedle array according to a fourth embodiment of the present invention.

Next, a fourth embodiment of the present invention will be explained with reference to FIG. 7. In the case of the second embodiment, the horizontal hole 29' is provided having an orifice only on one lateral side in the direction parallel to the bonding surface, and in the case of the fourth embodiment, penetrating holes are provided having orifices on both lateral sides in the direction parallel to the bonding surface. Moreover, the horizontal hole groove 29 is provided on the side of the second divisional element 5, similarly.

The other structure is substantially the same as that of the second embodiment as described above, so the same reference numerals will be allotted to the same parts in the drawing, and the explanation thereof will be omitted.

According to this structure, it is also possible to accomplish substantially the same effects as those of the second embodiment, and in addition, since there is a plurality of horizontal holes 29', provided also in the opposing directions, it is possible to further improve the efficiency in medical solution delivery.

Figure 8:
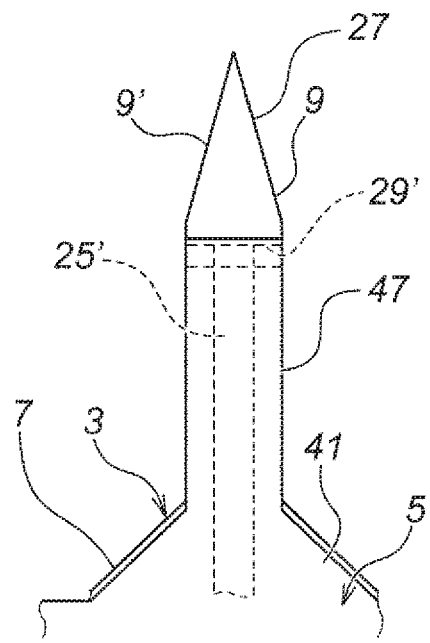
FIG. 8 is a partial front view of a microneedle array according to a fifth embodiment of the present invention.

Next, a fifth embodiment of the present invention will be explained with reference to FIG. 8. In the case of the fourth embodiment, the longitudinal passage groove 25 and the horizontal hole passage 29 are formed on the side of the second divisional element 5, and in the case of the fifth embodiment, the longitudinal passage groove 25 is formed on the side of the first divisional element 3, and the horizontal hole groove 29 is formed on the side of the second divisional element 5.

The other structure is substantially the same as that of the fourth embodiment as described above, so the same reference numerals will be allotted to the same parts in the drawing, and the explanation thereof will be omitted.

According to this structure, it is also possible to accomplish substantially the same effects as those of the fourth embodiment.

Figure 9A:
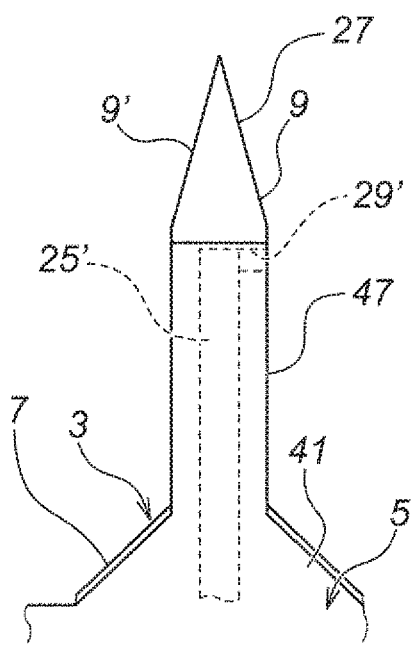
FIG. 9(a) is a partial front view of a microneedle array.
Figure 9B:
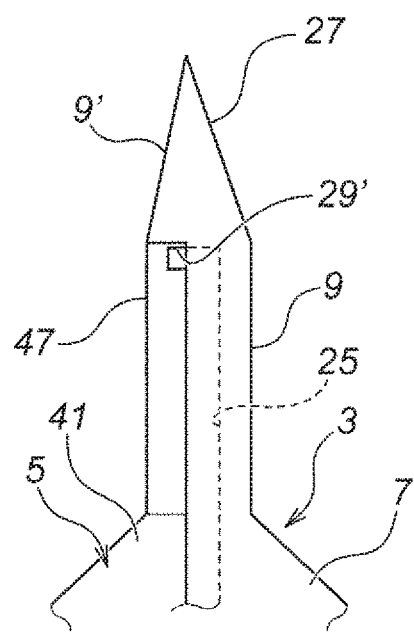
FIG. 9(b) is a partial side view of the same, according to a sixth embodiment of the present invention.

Next, a sixth embodiment of the present invention will be explained with reference to FIG. 9. In the case of the first embodiment, the longitudinal passage groove 25 and the horizontal hole passage 29 are formed on the side of the first divisional element 3, and in the case of the sixth embodiment, the longitudinal passage groove 25 is formed on the side of the first divisional element 3, and the horizontal hole groove 29 is formed on the side of the second divisional element 5.

The other structure is substantially the same as that of the first embodiment as described above, so the same reference numerals will be allotted to the same parts in the drawings, and the explanation thereof will be omitted.

According to this structure, it is also possible to accomplish substantially the same effects as those of the first embodiment.

Figure 10A:
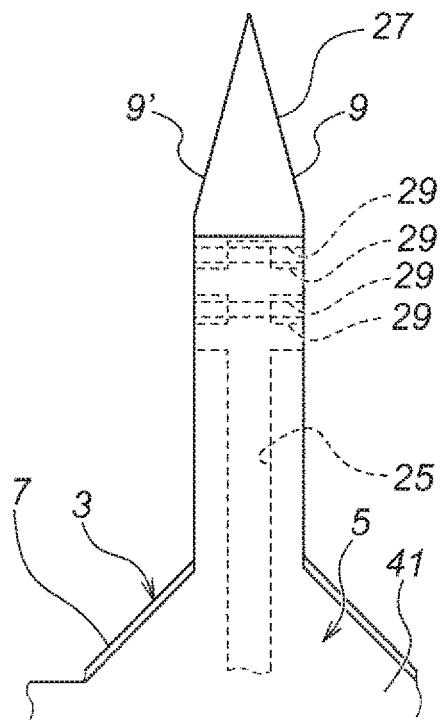
FIG. 10(a) is a partial front view of a microneedle array.
Figure 10B:
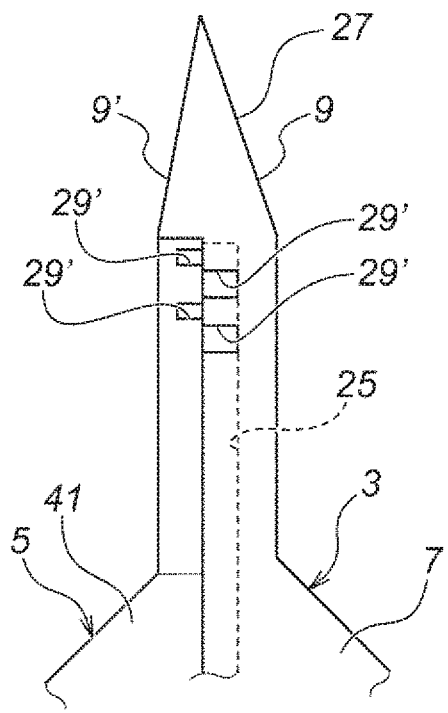
FIG. 10(b) is a partial side view of the same, according to a seventh embodiment of the present invention.

Next, a seventh embodiment of the present invention will be explained with reference to FIG. 10. In the cases of the first embodiment to the sixth embodiment, the explanation has been made wherein the horizontal hole 29' is provided at one position in the lengthwise direction of the microneedle 9', and in the case of the seventh embodiment, the explanation will be made wherein the horizontal holes 29' are formed at plural (in the present embodiment, four) positions, respectively.

Namely, on the side of the first divisional element 3, the longitudinal passage groove 25 is formed, and in addition, a plurality of (in the present embodiment, two) horizontal hole grooves 29 is also formed. On the other hand, on the side of the second divisional element 5, a plurality of (in the present embodiment, two) horizontal hole grooves 29 is formed. Thus, the horizontal hole grooves 29 on the side of the first divisional element 3 and the horizontal hole grooves 29 on the side of the second divisional element 5 are configured alternatively to form a staggered positioning. As a result, as illustrated in FIG. 10(*b*), the horizontal holes 29' are provided in the staggered positioning, at plural (in the present embodiment, four) positions in the elongating direction.

The other structure is substantially the same as those of the first embodiment to the sixth embodiment as described above, so the same reference numerals will be allotted to the same parts in the drawings, and the explanation thereof will be omitted.

According to this structure, it is also possible to accomplish substantially the same effects as those of the first embodiment to the sixth embodiment, and in addition, since there is a plurality of horizontal holes 29', provided also in the opposing directions, respectively, it is possible to further improve the efficiency in medical solution delivery.

Figure 11A:
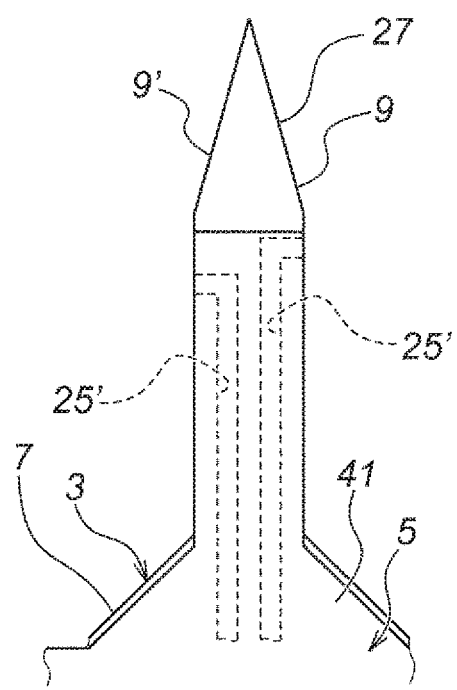
FIG. 11(a) is a partial front view of a microneedle array.
Figure 11B:
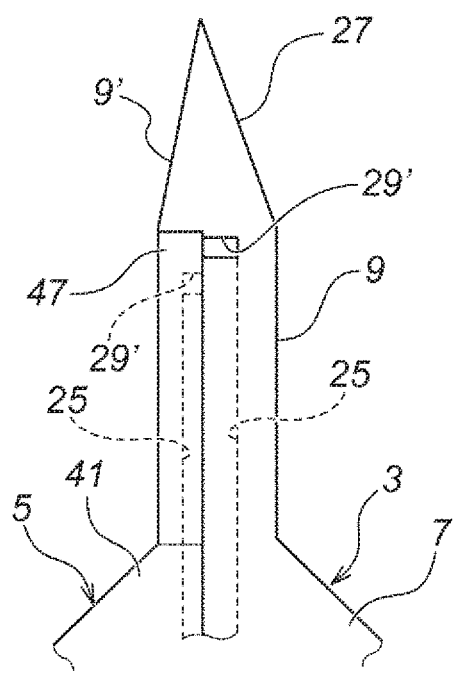
FIG. 11(b) is a partial side view of the same, according to an eighth embodiment of the present invention.

Next, an eighth embodiment of the present invention will be explained with reference to FIG. 11. In the case of the eighth embodiment, there is a longitudinal passage groove 25 on the side of the first divisional element 3, and there is another longitudinal passage groove 25 on the side of the second divisional element 5, and the respective tip parts of these two longitudinal passage grooves 25 are formed in an offset state. Moreover, one horizontal hole groove 29 is formed in the first divisional element 3. On the other hand, also one horizontal hole groove 29 is formed in the second divisional element 5. Thus, the horizontal hole groove 29 on the side of the first divisional element 3 and the horizontal hole groove 29 on the side of the second divisional element 5 are formed, respectively, at offset positions facing in the opposing directions. As a result, as illustrated in FIG. 11(*b*), the two horizontal grooves 29" are provided in the offset state facing in the opposing directions.

The other structure is substantially the same as those of the first embodiment to the seventh embodiment as described above, so the same reference numerals will be allotted to the same parts in the drawings, and the explanation thereof will be omitted.

According to this structure, it is also possible to accomplish substantially the same effects as those of the first embodiment to the seventh embodiment, and in addition, since there is a plurality of horizontal holes 29', provided also in the opposing directions, it is possible to further improve the efficiency in medical solution delivery.

Figure 12A:
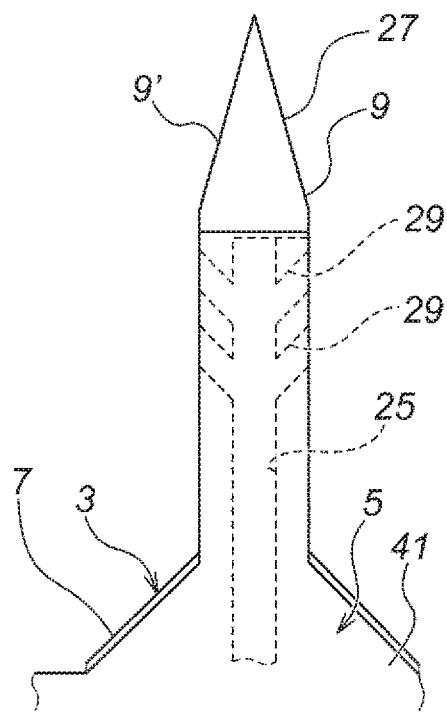
FIG. 12(a) is a partial front view of a microneedle array.
Figure 12B:
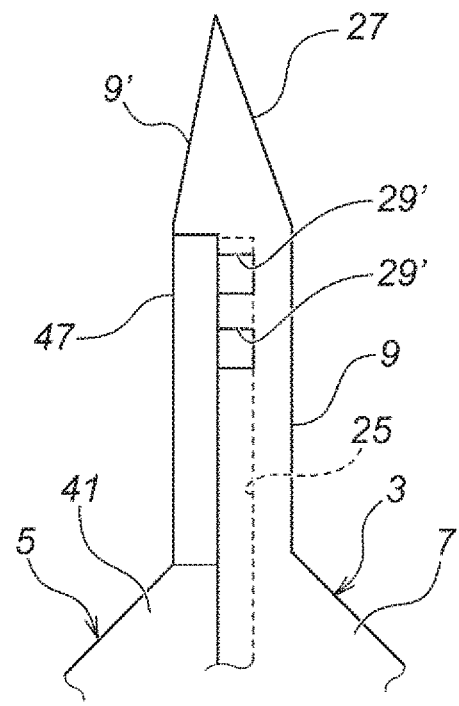
FIG. 12(b) is a partial side view of the same, according to a ninth embodiment of the present invention.

Next, a ninth embodiment of the present invention will be explained with reference to FIG. 12. In the case of the ninth embodiment, one longitudinal passage groove 25 is formed on the side of the first divisional element 3. Moreover, a plurality of (in the present invention, two on the right and two on the left, in total four) horizontal hole inclined grooves 29 is formed in the first divisional element 3. As a result, as illustrated in FIG. 12(*b*), two on the right and two on the left, in total four inclined horizontal holes 29' are provided.

The other structure is substantially the same as those of the first embodiment to the eighth embodiment as described above, so the same reference numerals will be allotted to the same parts in the drawings, and the explanation thereof will be omitted.

According to this structure, it is also possible to accomplish substantially the same effects as those of the first embodiment to the eighth embodiment, and in addition, since there is a plurality of horizontal holes 29', provided also in the opposing directions, it is possible to further improve the efficiency in medical solution delivery.

Figure 13A:
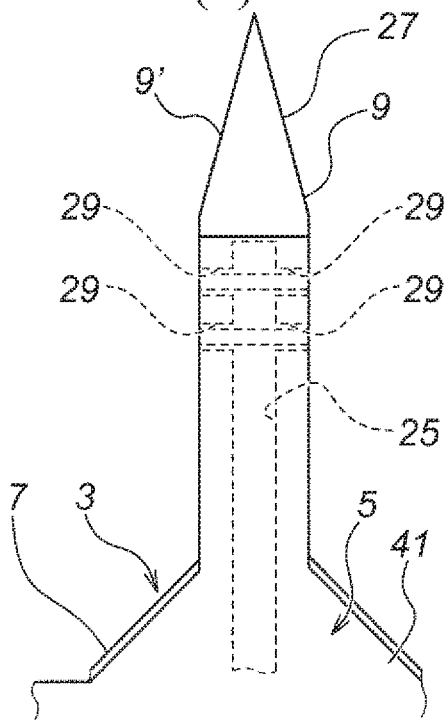
FIG. 13(a) is a partial front view of a microneedle array.
Figure 13B:
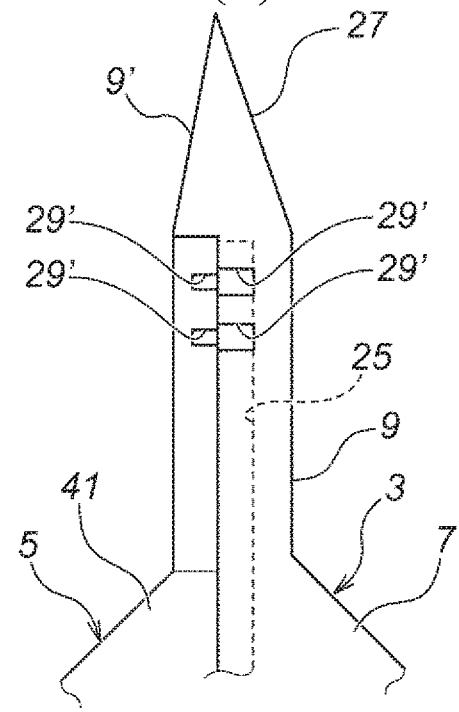
FIG. 13(b) is a partial side view of the same, according to a tenth embodiment of the present invention.

Next, a tenth embodiment of the present invention will be explained with reference to FIG. 13. In the case of the tenth embodiment, with regard to the structure of the seventh embodiment as described above, the horizontal hole groove 29 on the side of the first divisional element 3 and the horizontal hole groove 29 on the side of the second divisional element 5 are formed at the same position, without offset configuration.

The other structure is substantially the same as that of the seventh embodiment as described above, so the same reference numerals will be allotted to the same parts in the drawings, and the explanation thereof will be omitted.

According to this structure, it is also possible to accomplish substantially the same effects as those of the first embodiment to the ninth embodiment, and in addition, since there is a plurality of horizontal holes 29', provided also in the opposing directions, it is possible to further improve the efficiency in medical solution delivery.

Figure 14A:
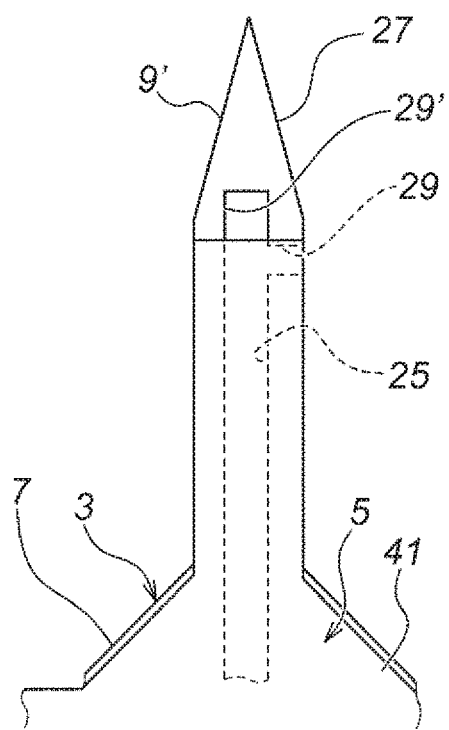
FIG. 14(a) is a partial front view of a microneedle array.
Figure 14B:
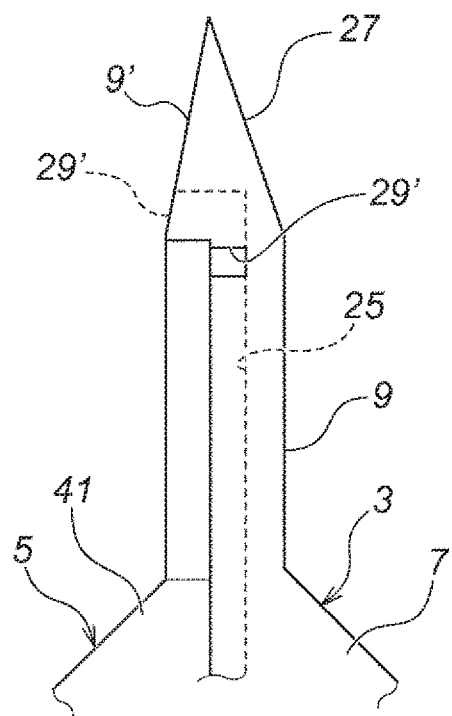
FIG. 14(b) is a partial side view of the same, according to an eleventh embodiment of the present invention.

Next, an eleventh embodiment of the present invention will be explained with reference to FIG. 14. In the case of the eleventh embodiment, there is the longitudinal passage groove 25 on the side of the first divisional element 3, and moreover, one horizontal hole groove 29 is formed in the first divisional element 3. The longitudinal passage groove 25 elongates upwardly at a predetermined amount, exceeding the top end of the second divisional element 5. As a result, as illustrated in FIG. 14(*b*), one horizontal hole 29' is provided, and in addition, one more horizontal hole 29' is provided in the direction intersecting with the bonding surface at an arbitrary angle.

The other structure is substantially the same as those of the first embodiment to the tenth embodiment as described above, so the same reference numerals will be allotted to the same parts in the drawings, and the explanation thereof will be omitted.

According to this structure, it is also possible to accomplish substantially the same effects as those of the first embodiment to the tenth embodiment, and in addition, since the horizontal hole 29' is additionally provided in the direction intersecting with the bonding surface at an arbitrary angle, it is possible to further improve the efficiency in medical solution delivery.

Next, a twelfth embodiment of the present invention will be explained with reference to FIG. 15. In the case of the twelfth embodiment, there are several limitations to the position of the horizontal hole 29' of the microneedle array 1 according to the first embodiment. The structure thereof will be explained in detail as below.

First, the structure of a skin S will be explained briefly. The skin S is composed of an intradermal portion $S_1$ and a subcutaneous tissue $S_2$, and the intradermal portion $S_1$ is composed of a keratin $S_{1-1}$, an epidermis $S_{1-2}$ and a dermis $S_{1-3}$. The intradermal portion $S_1$ is a region located about 2,000 μm intradermal from the surface. Moreover, the keratin $S_{1-1}$ is a region located about 20 μm intradermal from the surface, and the epidermis $S_{1-2}$ is a region located about 200 μm intradermal from the keratin $S_{1-1}$. Cells, such as immune cells, are concentrated in the region of the epidermis $S_{1-2}$, and capillary vessels are concentrated in the region of the dermis $S_{1-3}$. Moreover, lymphatic vessels are concentrated around the capillary vessels.

In the case of the present embodiment, the depth position of the horizontal hole 29' in a state that the microneedle array 1 is punctured, is located at an arbitrary position in the region within 2,000 μm intradermally, and more preferably, in the region within 1,000 μm intradermally, and especially preferably, in the region within 500 μm intradermally. With this structure, the medical solution can be fed to various cells such as immune cells, concentrating in the region of the epidermis $S_{1-2}$, and also to the lymphatic vessels around the capillary vessels, concentrating in the region of the dermis $S_{1-3}$.

The other structure is substantially the same as that of the first embodiment as described above, so the same reference numerals will be allotted to the same parts in the drawings, and the explanation thereof will be omitted.

With this structure as described above, the depth position of the horizontal hole 29' in a state that the microneedle array 1 is punctured into the skin S, is configured to be located at an arbitrary position in the region within 2,000 μm intradermally, and more preferably, in the region within 1,000 μm intradermally, and especially preferably, in the region within 500 μm intradermally, and therefore, it is possible to feed the medical solution efficiently, to various cells such as the immune cells, concentrating in the region of the epidermis $S_{1-2}$, and also to the lymphatic vessels around the capillary vessels, concentrating in the region of the dermis $S_{1-3}$.

For reference, in the case of a syringe needle 101, which is shown in FIG. 15 as a comparative example, because of the skill of a practitioner, the condition of the skin S, etc., it is difficult to locate a tip orifice 101*a* of the syringe needle 101 in a region within 2,000 μm intradermally, and in many cases, the tip reaches the subcutaneous tissue $S_2$. As a result, it is impossible to feed the medical solution efficiently, to various cells such as the immune cells, concentrating in the region of the epidermis $S_{1-2}$, and also to the lymphatic vessels around the capillary vessels, concentrating in the region of the dermis $S_{1-3}$.

Furthermore, it is possible to accomplish substantially the same effects as those of the first embodiment.

Next, a thirteenth embodiment of the present invention will be explained with reference to FIG. 16. In the case of the first embodiment to the twelfth embodiment, each of the longitudinal passages 25' of the plurality of (i.e. six) microneedles 9' is configured to be connected to the medical solution feeding passage 13 via the medical solution feed branching passages 17', 19', and in the case of the thirteenth embodiment, three medical solution feeding passages 13 are provided, whereby the longitudinal passages 25' of the two microneedles 9' are connected to one medical solution feeding passage 13 via the medical solution feed branching passages 17', 19'.

The other structure is substantially the same as that of the first embodiment as described above, so the same reference numerals will be allotted to the same parts in the drawing, and the explanation thereof will be omitted.

According to this structure, it is also possible to accomplish substantially the same effects.

Next, a fourteenth embodiment of the present invention will be explained with reference to FIG. 17. In the case of the first embodiment to the twelfth embodiment, each of the longitudinal passages 25' of the plurality of (i.e. six) microneedles 9' is configured to be connected to the medical solution feeding passage 13 via the medical solution feed branching passages 17', 19', and in the case of the fourteenth embodiment, two medical solution feeding passages 13 are provided, whereby the longitudinal passages 25' of the three microneedles 9' are connected to one medical solution feeding passage 13 via the medical solution feed branching passages 17', 19'.

The other structure is substantially the same as that of the first embodiment as described above, so the same reference numerals will be allotted to the same parts in the drawing, and the explanation thereof will be omitted.

According to this structure, it is also possible to accomplish substantially the same effects.

It should be noted that the present invention in not limited to the first embodiment to the fourteenth embodiment as described above.

First, the longitudinal passage groove and/or the horizontal hole groove may be arbitrarily formed in any one of the first divisional element and the second divisional element, and various combinations are available.

Similarly, it is also possible that the longitudinal passage groove and the horizontal hole groove are formed both in the first divisional element and the second divisional element. In this case, it is also possible to form them at the same position, or at any offset positions.

Moreover, in the first embodiment to the fourteenth embodiment, the explanation has been made in the case that the size of the horizontal hole is constant in the delivery direction of the medical solution. However, the present invention is not limited thereto, and for example, it is also possible to form that the size becomes gradually smaller toward an outlet. In this case, it is possible to further improve the efficiency in medical solution delivery.

Moreover, it is also possible to alter the depth and/or the width of the horizontal hole arbitrarily. With this structure, the delivery range of the medical solution may be adjusted.

Moreover, the position, number, direction of the horizontal hole(s) of each of the microneedles may be varied one by one.

Moreover, the length of each of the microneedles may be varied one by one, whereby the diffusion depth of the medical solution can be expanded.

Moreover, a plurality of microneedle lines, respectively composed of microneedles bonded to each other to form a line, may be configured, connected or communicated, so as to form an array.

Moreover, in the case that the additional horizontal hole is also provided in the direction intersecting with the bonding surface at an arbitrary angle, it is also possible to provide the horizontal holes at the time of forming of the respective divisional elements.

Further, the structures illustrated in the drawings are for the example purposes only.

INDUSTRIAL APPLICABILITY

The present invention relates to a microneedle array and a microneedle array manufacturing method, and more specifically, relates to those which improve medical solution delivery efficiency and facilitate manufacturing thereof, and the present invention is suitable, for example, for the microneedle array which injects various medical solutions subcutaneously.

EXPLANATION OF REFERENCE NUMERALS AND SIGNS

1 Microneedle Array
3 First Divisional Element
5 Second Divisional Element
7 Element Main Body
9 First Microneedle Element
9' Microneedle
25 Longitudinal Passage Groove
27 Tip Part
29 Horizontal hole Groove
25' Longitudinal Passage
29' Horizontal hole
41 Element Main Body
47 Second Microneedle Element

The invention claimed is:

1. A microneedle array comprising:
a first divisional element including a first element main body and a first microneedle element arranged on the first element main body;
a second divisional element bonded to the first divisional element, and including a second element main body and a second microneedle element arranged on the second element main body, the second microneedle element being bonded to the first microneedle element to form a microneedle;
a longitudinal passage formed between the first divisional element and the second divisional element bonded to each other; and
a horizontal hole, having an orifice opened in a horizontal direction parallel to a bonding surface of the first divisional element and the second divisional element bonded to each other, and communicating to the longitudinal passage,
wherein, the first microneedle element entirely includes a tip part of the microneedle having a complete arrowhead shape, and the second microneedle element has a length shortened by a length of the tip part of the microneedle,
the horizontal hole is formed between the first microneedle element and the second microneedle element at a side of the first element main body relative to the tip part of the microneedle having the arrowhead shape, and
the horizontal hole has another orifice opened in the horizontal direction parallel to the bonding surface to penetrate through lateral sides of the microneedle.

2. A microneedle array comprising:
a first divisional element including a first element main body and a first microneedle element arranged on the first element main body;
a second divisional element bonded to the first divisional element, and including a second element main body and a second microneedle element arranged on the second element main body, the second microneedle element being bonded to the first microneedle element to form a microneedle;
a longitudinal passage formed between the first divisional element and the second divisional element bonded to each other; and
a horizontal hole, having an orifice opened in a horizontal direction parallel to a bonding surface of the first divisional element and the second divisional element bonded to each other, and communicating to the longitudinal passage,
wherein, the first microneedle element entirely includes a tip part of the microneedle having a complete arrowhead shape, and the second microneedle element has a length shortened by a length of the tip part of the microneedle,
the horizontal hole is formed between the first microneedle element and the second microneedle element at a side of the first element main body relative to the tip part of the microneedle having the arrowhead shape, and
the horizontal hole includes a plurality of horizontal hole portions.

3. The microneedle array as claimed in claim 2, wherein, each of the plurality of horizontal hole portions is provided at a different position along a puncture direction.

4. The microneedle array as claimed in claim 2, wherein, the plurality of horizontal hole portions is formed in one microneedle.

5. The microneedle array as claimed in claim 4, wherein, the plurality of horizontal hole portions has orifices opened at lateral sides of the one microneedle in the horizontal direction parallel to the bonding surface.

6. A microneedle array comprising:
a first divisional element including a first element main body and a first microneedle element arranged on the first element main body;
a second divisional element bonded to the first divisional element, and including a second element main body and a second microneedle element arranged on the second element main body, the second microneedle element being bonded to the first microneedle element to form a microneedle;
a longitudinal passage formed between the first divisional element and the second divisional element bonded to each other; and
a horizontal hole, having an orifice opened in a horizontal direction parallel to a bonding surface of the first divisional element and the second divisional element bonded to each other, and communicating to the longitudinal passage,
wherein, the first microneedle element entirely includes a tip part of the microneedle having a complete arrowhead shape, and the second microneedle element has a length shortened by a length of the tip part of the microneedle,
the horizontal hole is formed between the first microneedle element and the second microneedle element at a side of the first element main body relative to the tip part of the microneedle having the arrowhead shape,
the first microneedle element includes a first straight portion extending from the first element main body, and an arrowhead portion having the arrowhead shape and connected to the first straight portion at a tip end of the first microneedle element,
the second microneedle element includes a second straight portion extending from the second element main body, and
the horizontal hole is formed between the first straight portion and the second straight portion.

7. The microneedle array as claimed in claim 6, wherein, the first microneedle element includes a plurality of first microneedle element portions on the first element main body and the second microneedle element includes a plurality of second microneedle element portions on the second element main body to form a plurality of microneedles.

8. The microneedle array as claimed in claim 7, wherein, lengths of the plurality of microneedles are ununified.

9. The microneedle array as claimed in claim 6, wherein, one of the first divisional element and the second divisional element includes a longitudinal passage groove, and another of the first divisional element and the second divisional element encloses the longitudinal passage groove to form the longitudinal passage.

10. The microneedle array as claimed in claim 6, wherein, the first divisional element and the second divisional element include longitudinal passage grooves, respectively, and the first divisional element and the second divisional element are bonded to each other to form the longitudinal passage.

11. The microneedle array as claimed in claim 6, wherein, one of the first divisional element and the second divisional element includes a horizontal hole groove, and another of the first divisional element and the second divisional element encloses the horizontal hole groove to form the horizontal hole.

12. The microneedle array as claimed in claim 6, wherein, the first divisional element and the second divisional element include horizontal hole grooves, respectively, and the first divisional element and the second divisional element are bonded to each other to form the horizontal hole.

13. The microneedle array as claimed in claim 6, wherein, the orifice is formed at a lateral side of the microneedle to be opened in the horizontal direction parallel to the bonding surface.

14. The microneedle array as claimed in claim 6, wherein, the orifice is formed on a lateral side of the microneedle to be opened in a direction intersecting with the bonding surface at an arbitrary angle.

15. The microneedle array as claimed in claim 6, wherein, the horizontal hole has a thickness gradually thinner toward the orifice.

16. The microneedle array as claimed in claim 6, wherein, the horizontal hole is oriented in an inclined direction, from a position orthogonal to the longitudinal passage, toward a tip side.

17. The microneedle array as claimed in claim 6, wherein, the horizontal hole is formed between the arrowhead portion and at least one of the first element main body and the second element main body.

18. The microneedle array as claimed in claim 6, wherein, the arrowhead portion protrudes from the first straight portion toward the second straight portion such that the second straight portion is arranged under the arrowhead portion, and
a bottom surface of the arrowhead portion contacts a top surface of the second straight portion to entirely cover the first straight portion and to open the orifice in the horizontal direction parallel to the bonding surface.

* * * * *